United States Patent [19]

Salditt et al.

[11] 4,112,177
[45] Sep. 5, 1978

[54] POROUS ADHESIVE TAPE

[75] Inventors: Ferdinand Salditt, Vallendar, Fed. Rep. of Germany; William L. Hansen, River Falls, Wis.

[73] Assignee: Minnesota Mining and Manufacturing Company, St. Paul, Minn.

[21] Appl. No.: 871,377

[22] Filed: Jan. 23, 1978

[51] Int. Cl.² ............................................. B32B 3/26
[52] U.S. Cl. .................................. 428/304; 128/156; 427/207 D; 428/354; 428/355; 428/356; 428/906
[58] Field of Search ............ 427/207 R, 207 B, 207 D; 128/155, 156; 428/304, 305, 354, 355, 356, 906

[56] References Cited

U.S. PATENT DOCUMENTS

| | | | |
|---|---|---|---|
| 2,328,057 | 8/1943 | Coulter | 428/351 |
| 2,328,066 | 8/1943 | Drew | 428/356 |
| 2,750,030 | 6/1956 | Tierney | 428/351 |
| 2,750,315 | 6/1956 | Tierney | 428/295 |
| 2,884,126 | 4/1959 | Ulrich | 428/355 |
| 2,897,960 | 8/1959 | Revoir | 428/353 |
| 3,121,021 | 2/1964 | Copeland | 428/219 |
| 3,876,454 | 4/1975 | Snell et al. | 428/355 |
| 4,061,826 | 12/1977 | Petras et al. | 428/356 |

*Primary Examiner*—William J. Van Balen
*Attorney, Agent, or Firm*—Cruzan Alexander; Donald M. Sell

[57] ABSTRACT

A microporous medical pressure-sensitive adhesive tape construction is provided having a plurality of layers of pressure-sensitive adhesive on a thin, uniformly porous backing wherein the total adhesive mass is microporous.

5 Claims, 2 Drawing Figures

POROUS ADHESIVE TAPE

This invention relates to a microporous pressure-sensitive adhesive tape or other pressure-sensitive coated sheet material capable of being wound in roll form having multiple pressure-sensitive adhesive layers covering one surface thereof.

It is well known in the prior art to anchor an adhesive layer to a backing by first coating the backing with a thin primer coating or layer. In such constructions, as exemplified in U.S. Pat. Nos. 2,328,057; 2,328,066; and 2,897,960, the layer in contact with the backing, generally referred to in the art as the "primer", is designed particularly to bond preferentially to the backing, so as to prevent offsetting of the adhesive when the tape is unwound. See, for example, U.S. Pat. No. 2,328,066; Pg. 1, Col. 2; line 36 to Pg. 2; Col. 1, line 6.

Pressure-sensitive tapes having more than one adhesive layer on the same side of the backing and in addition to a primer, if used, are also known in the prior art. See, for example, U.S. Pat. Nos. 2,750,030 and 2,750,315 to Tierney. In the constructions disclosed therein, lineally aligned monofilaments are sandwiched between the adhesive layers with the outer layer (farthest from the backing) serving as the functional layer.

In the early 1960's, a new kind of medical tape appeared in the marketplace, composed of an extremely thin tissue-like non-woven fabric backing composed of short discontinuous, randomly laid, highly flexible thin fibers sized with an acrylate water-repellent binder and having a thin acrylate adhesive layer coated on one surface thereof. The selection and treatment of the fibers and the amount of sizing in the formation of the backing is such that the resulting product is highly porous to air and has a light cloth-like hand and drape, resulting in high patient comfort, as contrasted, for example, with a heavy cloth or crinkly paper. The water insoluble acrylate adhesive is of sufficient thinness that the passage of moisture vapor therethrough is sufficiently unimpeded that when adhered to the skin of a patient the underlying skin does not macerate even though the tape may remain in place on the skin for days or even weeks. Further, by proper application, the adhesive layer, though visibly continuous upon casual inspection, is microporous throughout its volume to permit the passage of air therethrough over the entire surface of the adhesive. A basic teaching as to the formation of such a tape is found in U.S. Pat. No. 3,121,021.

This type of tape has found wide use in hospitals and has substantially replaced the previously used occlusive heavy cloth backed pressure-sensitive adhesive tape products. The present invention is an improvement on the basic tape construction of the lightweight porous pressure-sensitive adhesive tapes just described. This new tape provides greatly improved latitude in selecting desirable adhesive properties. While the acrylate adhesives used on these porous tapes at present are quite good in that they adhere well and comfortably as a general rule, remove readily and comparatively painlessly without leaving residue on the skin, and are hypoallergenic, they are applied in the form of a single thin layer. A typical class of these adhesives is described in U.S. Pat. No. 2,884,126.

In practice, the adhesive layer is applied to the tape backing by extruding or otherwise coating a solvent-containing solution or dispersion of the adhesive on a release liner in the form of a siliconized paper or the like, then either partially, or completely, removing the solvent to dry the adhesive sufficiently for transferring it by known means to the tape backing as a very thin layer whereupon small pores form in the dried adhesive on the backing.

We have now learned that the valuable properties of porous pressure-sensitive adhesive tapes can be maintained and the adhesive properties thereof enhanced by providing the adhesive as a plurality of layers. Further, this can be done even though the thickness of the adhesive is increased beyond the approximately 20 to 30 $g/m^2$ now generally found on the present single layer adhesive coated porous pressure-sensitive adhesive tapes.

A typical sheet material made in accordance with the present invention in tape form is shown in the accompanying drawings wherein.

Figure 1:
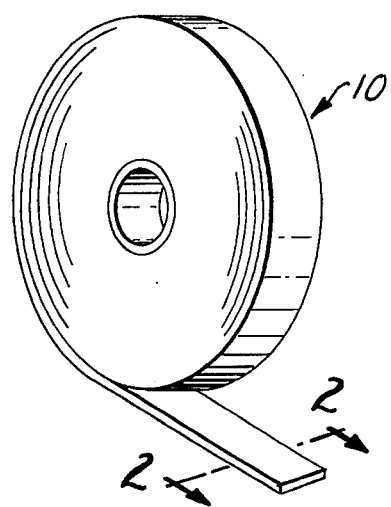
FIG. 1 is a roll of tape.

As depicted in FIG. 1 the adhesive coated sheet material is shown in the form of a roll of tape.

Figure 2:
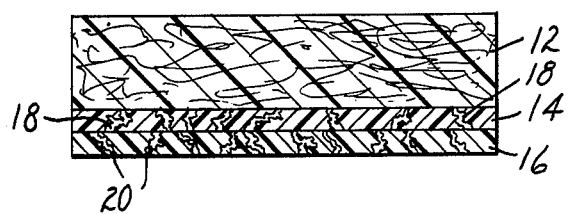
FIG. 2 is an enlarged cross-sectional view through the tape taken along section line 2—2 of FIG. 1.

In FIG. 2 the tape is seen to comprise a backing 12, a backing contacting adhesive layer 14 and a skin contacting adhesive layer 16. Layers 14 and 16 are provided with microporously sized pores 18 and 20 therethrough.

One way of carrying out our invention is to place a thin layer of pressure-sensitive adhesive on a smooth surfaced release liner, dry it, next apply a second thin layer of an adhesive over the first layer, then laminate the multilayered adhesive to the porous backing with subsequent removal of the release liner. The layer that contacts the surface of the tape backing during lamination (the second layer on the release liner) is of a kind and of a thinness which ordinarily develops pores after such lamination while the other layer (the first on the liner), which in the finished tape provides the exposed adhesive surface (the overlying layer), will likewise develop pores. The first layer is preferably somewhat thinner and softer than the second although there may be tape constructions where this relationship need not be followed.

It is surprising that the entire structure becomes porous, since the first layer coated on the liner shows no evidence of porosity prior to the laminating step.

For consistency and simplicity, the layer first coated on the liner, and contacting the skin when the tape is used, will be referred to herein as the "skin layer", while the other layer which contacts the backing when the tape is in use will be referred to as the "backing layer".

Because of its simplicity, the method described above is generally preferred. Another procedure is to actually build the multiple adhesive layers on the backing. The backing layer of adhesive may be laminated to the backing from a release liner and dried, if not already dried before laminating. Thereafter, the skin layer of adhesive, which may be different from the first, and on its own release liner, is laminated to the backing layer.

Other known transfer procedures will suggest themselves to those skilled in the art, and obviously more than two layers of adhesive may be laminated to one another in the formation of the final adhesive mass on the tape backing. However, rarely should more than two layers be required. As for the release liner, it may be in the form of a strip, belt, drum or the like, depending on the equipment requirements of the tape manufacturer. See, for example, U.S. Pat. No. 3,121,021, col. 4, lines 3–33.

Acrylate adhesives are capable of being formulated to provide rubbery, polymeric, hydrophobic adhesives throughout a very broad spectrum of properties. They may be crosslinked, i.e., by covalent bonding or by hydrogen bonding, or they may be free from cross-linking. In general, the greater the cross-linking, the more firm the adhesive. These adhesives may be formulated to provide very firm or very soft rubbery layers with varying degrees of adhesive and cohesive properties, but like all pressure-sensitive adhesives they are viscoelastic materials. Unlike rubber based pressure-sensitive adhesives, the acrylate adhesives may be used significantly free of additives which may cause skin irritation.

While preferred adhesive masses for medical tapes are those comprising multi-layers of acrylate adhesives having different properties, the adhesive layers may nevertheless be of different classes of adhesive. Thus, for example, the backing layer may, for economical or other reasons, be composed of a rubber resin based pressure-sensitive adhesive and the skin layer may be a hypoallergenic acrylate adhesive.

EXAMPLE 1

A specific porous pressure-sensitive medical adhesive tape of this invention is one wherein the backing adhesive layer, comprises a relatively firm acrylate adhesive coated to a dried layer weight of approximately 23 g/m$^2$ with a much softer skin adhesive layer having a dried layer weight of approximately 4 g/m$^2$. The backing is that described in Example 1 of U.S. Pat. No. 3,121,021 and the adhesive layers are provided from siliconized release paper following the general procedures of that example.

The backing layer is an acrylate copolymer comprising, in parts by weight:
Isooctyl acrylate — 94
Acrylic acid — 6
dispersed in a mixture of:
n-heptane — 70
Isopropanol — 30
to approximately 20% solids by weight.

The skin layer comprises the same basic adhesive as above, with the addition to the adhesive of 40% by weight of a tackifier resin, e.g., glycerol ester of hydrogenated rosin marketed as "Foral 85" by Hercules Incorporated, resulting in an adhesive dispersion of about 28% solids. The addition of the tackifier provides a demonstrable improvement in adhesion to skin.

The tape of the above example has a porosity, measured in the Gurley densometer, of 1455 seconds and adhesion values, as measured by procedures set forth in *Test Methods for Pressure Sensitive Tapes* (Pressure Sensitive Tape Council, Glenview, Ill.) of 525 gm per 2.54 cm width to a steel plate; 680 gm to glass; and 45 gm to human skin.

The adhesion to skin is measured as follows:
(1) Tape samples, 2.54 cm wide by approximately 5.08 cm long, are placed on the back of a human subject.
(2) Each tape is rolled down with one forward and one reverse pass of 1 kg tape roller moved at a rate of about 30 cm per minute. The roller used is of the type described in *Test Methods for Pressure Sensitive Tapes*, Appendix B, Sections 2.7.1; 2.8.1; and 2.8.2.
(3) Adhesion to skin is measured by 180° peel type removal. The peel force values are measured through the use of a strain gauge mounted on a motor driven carriage. The force of removal is reported in grams of adhesion per 2.54 cm width of sample. The rate of removal is 15 cm per minute. This dual layered adhesive mass thereby is provided with a firm underlying layer which preserves the porous nature of the adhesive mass and a "quickstick" softer outer layer of adhesive which adheres very readily to the skin.

Use of the soft, tackified mass as the entire adhesive coating tends to produce a tape where the adhesive oozes from the edges of the tape in roll form, as is well known in the tape art. Further, if the adhesive flows, because of its softness, the tape, after standing for a time in roll form, may lose porosity, the adhesive blocking the pores in the backing. The firm backing mass eliminates this, yet the tackified, softer, skin layer provides excellent functional adhesion.

In the following tabulated examples, the adhesive compositions are represented by letters which have the following significance:
A. The backing adhesive of Example 1
B. The skin adhesive of Example 1
C. A water based thermoplastic polymeric acrylate adhesive of approximately 65% n-butylacrylate and 35% n-butyl methacrylate (marketed by Rohn & Haas as "N 560")
D. A natural, rubber-resin adhesive, comprising in parts by weight:

| | |
|---|---|
| Natural rubber latex | 100 |
| Tackifier, β-pinene polyterpene, marketed as "Piccolyte S115"by Hercules | 75 |
| Antioxidant, 2,4-di(tertiary-amyl) hydroquinone, marketed as "Santovar A: by Monsanto | 1.0 |
| Cyclohexylamine | 0.2 |
| Heptane - to give normal coating viscosity (20% solids) | |

E. A water based rubber latex adhesive comprising:
A blend of 60% solids natural rubber latex, ammonia preserved, and a 40% solids emulsion of the glycerol ester tackifier resin previously described herein.
The tackifer resin emulsion was prepared by dissolving the tackifier resin in toluene and then using a fatty acid soap system to bring about the emulsification. This resin emulsion was then blended with natural rubber latex at a ratio of about 60% rubber solids and 40% resin solids to 50% solids water based adhesive.

| | Experiment Number | | | | |
|---|---|---|---|---|---|
| | 1 | 2 | 3 | 4 | 5 |
| | A | B | C | D | E |
| Backing layer-GMS/SQ. M. | —* | 20C | —* | 23E | 23D |
| Skin layer-GMS/SQ. M. | 27A | 4B | 27E | 4B | 4B |
| Total Coating Weight-GMS/SQ. M. | 27 | 24 | 27 | 27 | 27 |
| Porosity (seconds) | 180 | 14 | 780 | 1800 | 1200 |
| Adhesion/Steel GM/2.54 CM | 539 | 624 | 226 | 709 | 397 |
| Adhesion/Glass GM/2.54 CM | 652 | 454 | 482 | 793 | 709 |
| Adhesion/Skin GM/2.54 CM | 73 | 58 | 27 | 72 | 39 |

*Single layer construction

The benefits of the invention can be seen from the above results, which are now explained in some detail. Gurley densometer readings of greater than about 4000 seconds are considered substantially non-porous for purposes of this invention.

Experiment 1 is a "standard" microporous tape, such as taught by the Copeland patent, U.S. Pat. No. 3,121,021.

Experiment 2 is a tape utilizing the teachings of our invention. The backing adhesive, however, is, as noted hereinbefore, a water based acrylate. The use of water based adhesives is highly desirable, eliminating as it does the waste of hydrocarbon solvents, and lessening pollution problems. Further, such adhesives are generally more firm than solvent-based adhesives and thus are believed to maintain porosity more readily over extended periods of time. The very thin skin layer, however, coated from solvent, while non-porous upon microscopic examination, becomes porous after contacting the backing layer and drying of the backing layer in contact with the non-woven adhesive tape backing.

Similar advantages can be seen by comparing Experiments 3 and 4. Experiment 3 is a microporous tape using the teachings of U.S. Pat. No. 3,121,021 and, while its porosity and adhesion values are acceptable, it is made from a natural rubber latex, with a tackifier resin. This has the advantage of avoiding organic solvents, and also offers considerable economic advantage over the acrylates, but, being potentially more irritating to the skin, is a step backward in the surgical adhesive art. By the use of our invention, however, utilizing a thin layer of an acrylate as a skin adhesive, and the rubber resin as a "bulk" backing adhesive, a satisfactory tape, having improved adhesive properties, is obtained, although there is a sacrifice in porosity. However, it should be again noted that the dried skin adhesive layer was not porous prior to the final laminating step.

A further example is provided in comparing Experiments 1 and 5, which show that a tape having properties comparable to the "standard" (except for a decrease in porosity) can be made using a relatively economical solvent based rubber-resin adhesive, well known over many years to those skilled in the art, as the backing adhesive, with a thin layer of acrylate to provide the beneficial non-irritating properties as the skin adhesive.

The loss of porosity in some cases is not understood. It is not universal, as inspection of Experiment 2 reveals. It may be due to variations in coating conditions not sufficiently understood at this time. In the case of Experiments 3 and 4, the porosity could possibly be improved by utilizing the teachings of U.K. Pat. No. 799,424.

While the foregoing examples have utilized a solvent coated skin layer and a water-based backing layer of adhesive, the same general results are achieved by utilizing water-based adhesives in both layers, even though water-based adhesives are normally not as sticky to the touch and for that reason are not usually preferred as the skin layer. Nevertheless, water-based adhesives can be made in varying degrees of softness and/or firmness such that the skin contacting layer may be quite soft and therefore more compliant than the backing layer with consequently greater thumb appeal, or quickstick adhesive properties. To make such a product following the teachings of U.S. Pat. No. 3,121,021, however, it is necessary that the silicone liner on which the skin layer is to be cast be made water receptive either by the addition of a primer thereto or by formulation of the skin layer adhesive to enable the adhesive itself to properly wet the carrier surface. Regardless of the way in which the layers are provided in the composition of the two or more layers of the product, this invention paves the way for providing a soft, conformable sticky skin layer to provide good quick tack properties while the backing layer confers porosity and cushioning to aid in conformability of the tape against the skin.

This invention is of particular interest with respect to the manufacture of porous medical pressure-sensitive adhesive tapes where adhesive compositions are applied to a non-woven backing so that the adhesive composition also becomes porous. This new process permits the manufacture of such adhesive tapes having greater adhesive strength yet great skin affinity than has heretofore been possible. For example, in the past it has not been practical to coat very soft skin specific adhesives while avoiding oozing and edge tackiness in the rolls, and ultimate loss of porosity, whereas with this new multiple layer adhesive application method, soft skin adhesive masses can be used without significantly detracting from the over-all adhesive firmness of the tape. The present process enables the creation of an adhesive underlying layer of optimum porosity formation and maintenance coupled with the formation of an overlying skin adhering adhesive layer of greatly improved quality, along with the possibility of an over-all increase in coating thickness which may be necessary in specific applications.

That which is claimed is:

1. A process for making a microporous pressure-sensitive adhesive coated sheet material comprising the steps of: (1) providing a first substantially dry thin layer of a pressure-sensitive adhesive on a smooth release surface; (2) coating at least one further layer of an adhesive composition onto said first adhesive layer; (3) partially drying said further adhesive layer; (4) contacting the exposed surface of said further layer with the surface of a thin uniformly porous backing, and (5) laminating the backing to the adhesive layers whereupon the adheisve mass develops microporosity throughout its thickness and over its area of contact with the substrate.

2. A microporous pressure-sensitive adhesive coated sheet material comprising a thin substantially uniformly porous substrate having firmly anchored to one major surface thereof a thin adhesive mass composed of a plurality of normally tacky and pressure-sensitive adhesive layers, said adhesive mass being microporous throughout and the layer of said adhesive mass farthest from said substrate comprising a soft rubbery acrylate copolymer.

3. Microporous sheet material according to claim 2, characterized in that the layer of adhesive anchored to the substrate is coated from water.

4. Microporous sheet material according to claim 2, characterized in that the layer of adhesive anchored to the substrate is a blend of natural rubber.

5. Microporous sheet material of claim 2 wound in roll form as a pressure-sensitive adhesive tape.

* * * * *